United States Patent [19]

Traina

[11] Patent Number: 4,937,461
[45] Date of Patent: Jun. 26, 1990

[54] TRANSMISSOMETER HAVING SOLID STATE LIGHT SOURCE

[76] Inventor: John E. Traina, 303 N. Rose Dr., Glenshaw, Pa. 15116

[21] Appl. No.: 234,428

[22] Filed: Aug. 22, 1988

[51] Int. Cl.⁵ .......................................... G01N 21/59
[52] U.S. Cl. ................................. 250/575; 356/437; 356/438; 250/205
[58] Field of Search ............... 250/573, 575, 576, 205; 356/434, 435, 436, 437, 438, 439, 440, 441, 442

[56] References Cited

U.S. PATENT DOCUMENTS 3,917,957 11/1975 Ansevin et al. ...................... 356/436
4,249,244 2/1981 Shofner et al. ...................... 250/573
4,589,775 5/1986 Milhous, Jr. et al. ............... 356/440

Primary Examiner—Edward P. Westin
Attorney, Agent, or Firm—Buchanan Ingersoll

[57] ABSTRACT

An improved transmissometer and optical assembly therefor contains a solid state light source preferably a light emitting diode. The ligh source emits a low level light beam that is split, part of which is passed through a gaseous sample then directed to a detector while the otehr part is directed to a second detector. Electronic components are provided to use signals from the detectors to control the light source and determine opacity of the sample.

16 Claims, 2 Drawing Sheets

TRANSMISSOMETER HAVING SOLID STATE LIGHT SOURCE

FIELD OF INVENTION

This invention generally relates to transmissometers of the type wherein the density, transmission or opacity of a gaseous sample is measured as a function of the attenuation of a light beam passed through the sample. This invention relates to transmissometers which are used for measuring density, transmission or opacity of stacks or ducts which contain the gases resulting from burning fossil fuel.

DESCRIPTION OF THE PRIOR ART

The use of optical devices to measure the density or opacity of gaseous materials, smoke for example, is known in the art. Examples may be seen in U.S. Pat. Nos. 3,600,590; 3,617,756; 3,810,697 and 3,917,957.

Typically one type of transmissometer is comprised of an optical assembly having a light source which emits a light beam. The light beam is split with one portion being directed to a reference detector and the remaining portion being directed through a sample to a retro-reflector. The retro-reflector reflects the light beam back through the sample to a signal detector. The light beam striking the signal detector is compared electronically to the light beam striking the reference detector to determine opacity.

The transmissometers of the prior art for stacks and ducts all use a tungsten incandescent light bulb as the light source. Consequently, the light source is relatively large and needs substantial electrical power. Other shortcomings of light bulbs as light sources are that the associated electrical components such as the socket, transformer and wiring are heavier and less rugged as compared to a solid state light source configuration; light bulbs give off heat; light bulbs have a shorter life; light bulbs require spectral filters to meeting EPA color requirements and light bulbs cannot be directly modulated effectively.

Prior to the present invention the art believed that light emitting diodes and other low power light sources could not be used in a transmissometer because the light beam which they produce is too dim to operate over the general application requirement for stacks and ducts ranging from 0.5 feet to 30 feet separate between the optical assembly and retro reflector. Consequently, the compact size and low power requirements of diodes and other advantages are not available in prior art transmissometers.

Consequently, there is a need for a transmissometer which has a solid state light source.

The Environmental Protection Agency has established standards for transmissometers which are set forth in Title 40, Code of Federal Regulations, Part 60, Appendix B. Many users will not buy a transmissometer which does not meet these standards. Consequently, it is advantageous for a transmissometer to meet these standards.

SUMMARY OF THE INVENTION

My improved transmissometer contains a solid state light source which requires low power, is lighter and more rugged and gives off low heat, has longer life and can be directly modulated and meets the requirements of 40CFR60 Appendix B. In this general class of transmissometer, a light beam, modulated at a pre-selected frequency, is passed through a gaseous sample.

In my apparatus the light source is modulated and then split. One portion goes to a reference detector and the second portion passes through the sample. This second portion is reflected back through the sample by a retro-reflector positioned across the sample from the source of the modulated beam. The components of the improved transmissometer include a light emitting diode and associated circuitry which generates a light beam that passes through and is reflected back through a sample.

DESCRIPTION OF THE PREFERRED EMBODIMENTS

Figure 1:
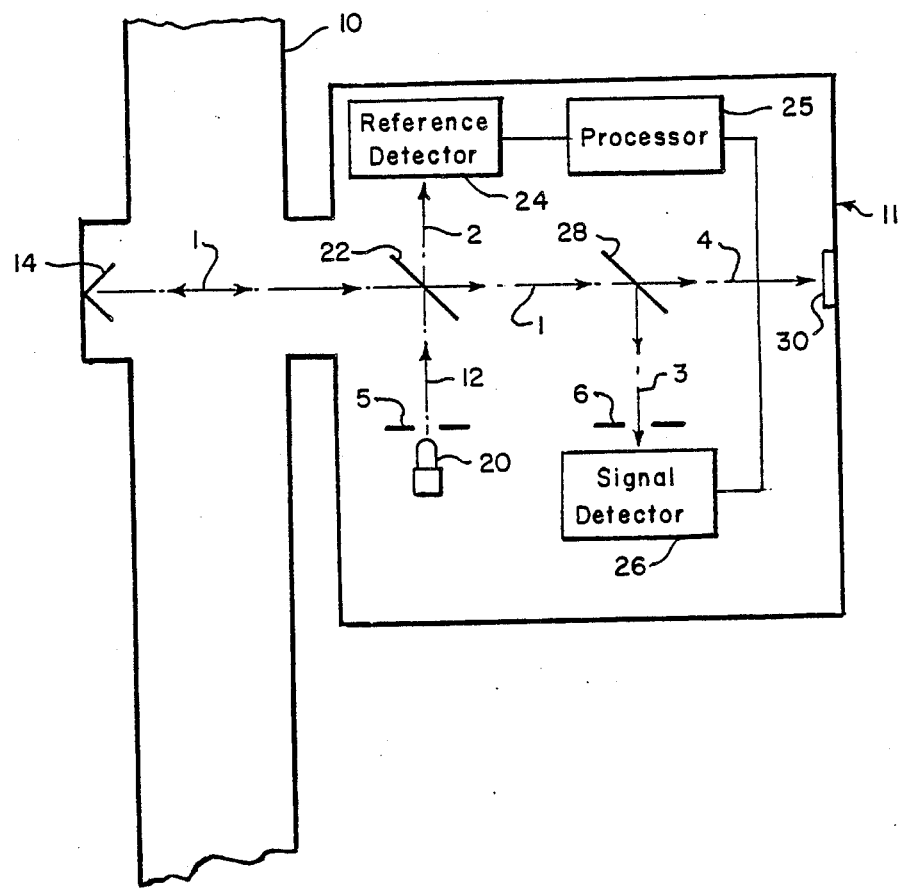
FIG. 1 is a schematic diagram of a transmissometer which may contain my improved optical assembly.

FIG. 1 shows a configuration of a double pass transmissometer connected to a conduit 10 through which a gaseous sample passes. The transmissometer is comprised of an optical assembly 11 which produces a light beam 1 that passes through the gaseous sample in conduit 10 and is reflected by retro-reflector 14 to the optical assembly 11. Within the optical assembly 11 is a light source 20 which produces a light beam 12. The light beam 12 travels through the projection aperture 5 to a beam splitter 22 which splits beam 12 into a first light beam 1 and a second light beam 2. The second light beam 2 is directed to a reference detector 24 which translates the light beam 2 into an electrical signal. The first light beam 1 is reflected from retro-reflector 14 to a signal detector 26. If desired, the reflected beam 1 may be split by beam splitter 28 into a third light beam 3 and a fourth light beam 4. The third light beam 3 is directed through field stop 6 to a signal detector 26 and the fourth beam 4 is directed to a window 30. The signal detector 26 converts the third beam 3 into an electrical signal. A processor 25 or other comparable circuitry receives the electrical signals from detectors 24 and 26 and compares them. Since the signal from reference detector 24 corresponds to a light beam that has not passed through the sample, and the signal from signal detector 26 corresponds to a light beam that has passed through the sample, a comparison of the two signals can reveal the opacity of the sample. Although I prefer to provide a retro-reflector to reflect the light beam back through the sample, such a double pass arrangement is not necessary to my invention. A single pass configuration can be obtained by placing signal detector 26 in the position of retro-reflector 14.

Within the optical assembly lenses can be used to focus the various light beams. For ease of illustration, I have not shown any such lenses but those skilled in the art will recognize that such lenses could be and commonly are used. I have also not shown chopping means such as that taught in my U.S. Pat. No. 3,917,957. However, it should be understood that chopping means could be used.

Figure 2:
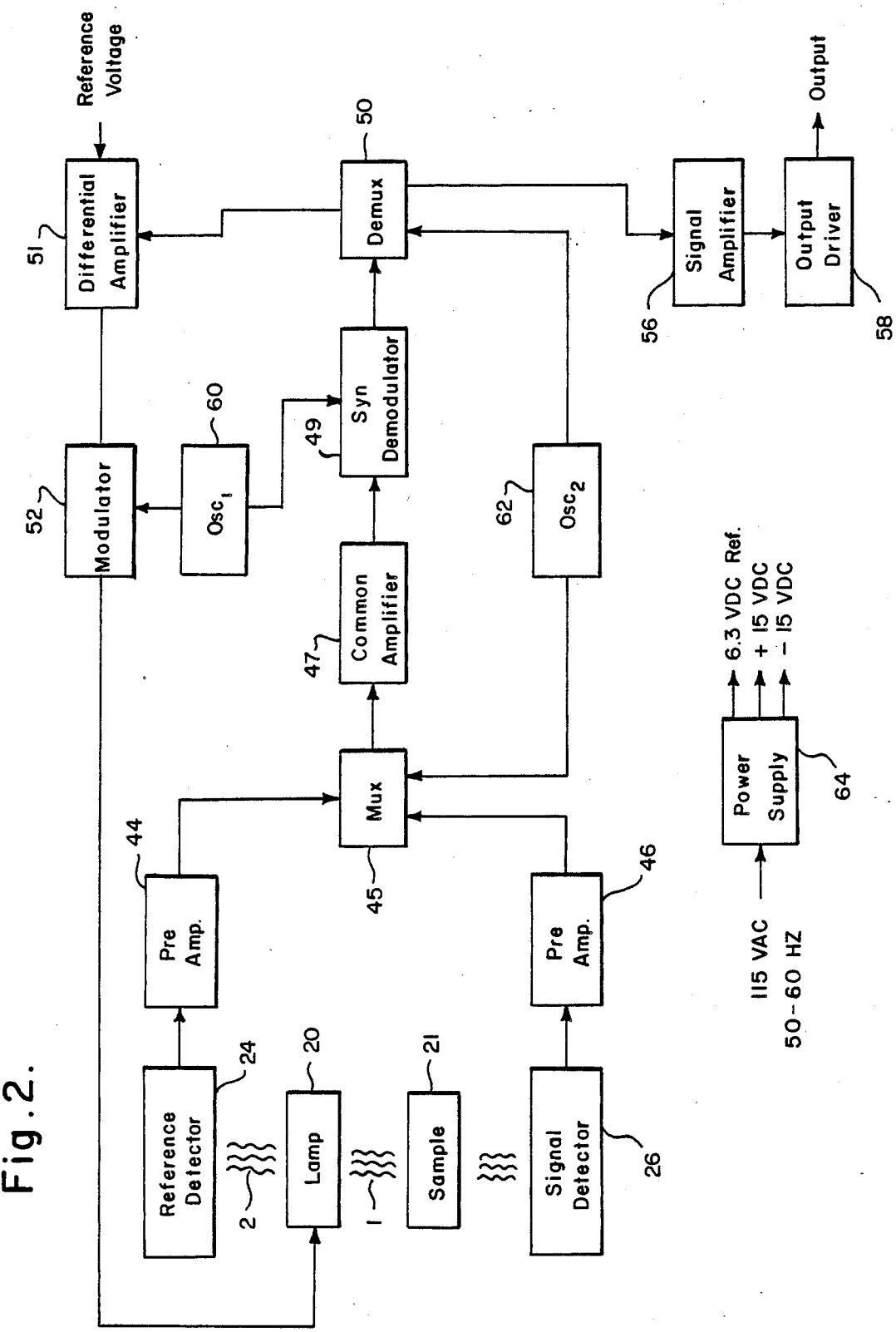
FIG. 2 is a block diagram of my improved optical assembly.

In the transmissometer of the prior art light source 20 is a tungsten incandescent light bulb. However, I have found that the circuitry and components diagramed in FIG. 2 will permit the use of a light emitting diode. Moreover, the entire light source and components of FIG. 2 can be assembled into a solid state circuit which can be more simply powered. The circuitry of FIG. 2 is intended to be used in a transmissometer of the type illustrated in FIG. 1. Most of the components of the circuit of FIG. 2 would be included in the circuitry identified by box 25 of FIG. 1. Where like components appear in both figures, I have used the same reference number.

Referring to FIG. 2, I provide a light source 20 which produces light beams 1 and 2. The first light beam passes through the sample 21 and is reflected to signal detector 26. The second beam is directed to reference detector 24. The detectors 26 and 24 generate electrical signals that correspond to the light beams 1 and 2 which they receive. The signals pass through preamplifiers 44 and 46 to multiplexer 45. The multiplexer 45 alternatively sends the reference signal and the sample signal to a common amplifier 47. The common amplifier 47 sends the amplified signals to a synchronous demodulator 49. The demodulator 49 removes the carrier portion from the signals and supplies the signals alternatively to a demultiplexer 50. The signals are then separated and the reference signal is sent to a differential amplifier 51. In this amplifier the reference signal is compared against a reference voltage of preferably 6.3 volts. The output of the differential amplifier 51 will continually change until the reference signal from the demultiplexer 50 exactly equals a reference voltage. The differential amplifier output feeds a modulator 52. I prefer to provide an oscillator 60 to provide a carrier signal to the modulator 52. In the modulator 52, the off/on signal of the carrier is controlled in amplitude by the signal from the differential amplifier 51. The modulator drives the light source 20 which completes the loop. The result of this loop is a constant level amplitude modulated light output from the light source.

The sample signal which is generated by sample detector 26 is processed in the same manner as the reference signal until it reaches demultiplexer 50. The demultiplexer 50 sends the sample signal straight to a signal amplifier 56 and output driver 58 for gauges or other indicators (not shown). These devices create a display such as a number or a graph which tells the operator about the opacity of the sample. With the light source output held constant by the reference loop, the signal reaching the signal amplifier will only change if the sample path changes its attenuation.

The adjustments in the signal amplifier and output drive are used to typically set the output to 20 ma with no attenuation (0% opacity) and 4 ma with the light blocked off completely (100% opacity).

There are two oscillators 60 and 62 in the unit. One provides the carrier signal at 2.5 KHZ, the other provides the multiplex/demultiplex control signals.

The power supply 64 provides three regulated DC voltages as shown. The 6.3 volts is the reference voltage and is temperature compensated. The 63 reference voltage is applied to differential amplifier 51. The positive and negative 15 volt terminals connect to and power the detectors 24 and 26 and can power other components in the system.

I have found that the following components can be used in my circuit:

| Reference No. | Description | Part No. | Supplier |
|---|---|---|---|
| 20 | LED | ESPY-5701 | A. C. Interface |
| 24 and 26 | Detectors | PIN 5DP | United Detector |

-continued

| Reference No. | Description | Part No. | Supplier |
|---|---|---|---|
| 44 and 46 | Pre-amp | LF 257H | National Sem. |
| 45 | Multiplexer | IT400 A | Intersil |
| 47 | Amplifier | LF257H | National Sem. |
| 49 | Demodulator | 3510A M | Burr-Brown |
| 50 | Demultiplexer | IH401AE | Intersil |
| 57 | Differential Amp. | TLO84CN | Texas Instruments |
| 52 | Modulator | IT400A | Intersil |
| 56 | Amplifier | TLO84CN | Texas Instruments |
| 53 | Oscillators | CD4047BE | RCA |

When fully assembled my optical assembly and the transmissometer which contains this assembly, are rugged precision, electro-optic instruments. The transmissometer will meet or exceed the current standards reported in Title 40 of the Code of Federal Regulations at Part 60, Appendix B.

While I have shown and described certain present preferred embodiments of my invention, it should be distinctly understood that the invention is not limited thereto, but may be variously embodied within the scope of the following claims.

I claim:

1. An improved optical assembly which produces a light beam for a transmissometer of the type wherein the light beam is passed through a gaseous sample, the assembly comprised of:

(a) a solid state light source which emits a light beam;

(b) a reference detector which converts a light beam to an electrical signal;

(c) a signal detector which converts a light beam to an electrical signal;

(d) a beam splitter sized and positioned to split the light beam into a first beam and a second beam, to direct the first beam to the reference detector, and to direct the second beam through the sample to the signal detector;

(e) a preamplifier connected to the reference detector and a second preamplifier connected to the signal detector to receive an electrical signal therefrom which amplifies the electrical signal;

(f) a multiplexer connected to the preamplifier which alternatively send a signal received through the preamplifier from the reference detector and a signal received through the second preamplifier from the signal detector;

(g) an amplifier connected to receive signals from the multiplexor;

(h) a demodulator connected to receive signals from the amplifier and remove a carrier portion from the signals;

(i) a demultiplexer connected to receive signals from the demodulator and which separates the signals;

(j) a differential amplifier connected to receive signals from the demultiplexor and which compares the received reference signal to a reference voltage and produces an output signal which will continually change until a reference signal is received from the demultiplexer which equals the referene voltage;

(k) a modulator connected to receive a signal from the differential amplifier and having an output which is connected to the light source in a manner so that the output from the modulator determines intensity of the light beam emitted by the light source;

(l) a signal amplifier connected to the demultiplexer for receiving a signal from the demultiplexer corresponding to the opacity of the sample; and (m) output means connected to receive a signal from the signal amplifier and create s display corresponding to the signal in a manner selected by an operator to tell the operator the capacity of the sample.

2. The improved assembly of claim 1 also comprising a retro-reflector positioned to reflect the second beam back through the sample to the signal detector.

3. The improved assembly of claim 1 also comprising a second oscillator connected to the demultiplexer.

4. The improved optical assembly of claim 1 also comprising a window and a second beam splitter positioned to receive the second beam from the sample and split the second beam into a third beam which is directed to the signal detector and a fourth beam which is directed to the window.

5. The improved optical assembly of claim 4 wherein the second beam splitter is an 80/20 beam splitter.

6. The improved optical assembly of claim 1 wherein the beam splitter is a 50/50 beam splitter.

7. The improved optical assembly of claim 1 wherein the light source is a light emitting diode.

8. The improved assembly of claim 1 also comprising an oscillator connected to the modulator and demodulator.

9. An improved transmissometer of the type wherein a light beam is produced by an optical assembly passed through a gaseous sample, to at least one detector wherein the improvement comprises:

(a) a solid state light source which emits a light beam;

(b) a reference detector which converts a light beam to an electrical signal;

(c) a signal detector which converts a light beam to an electrical signal;

(d) a beam splitter sized and positioned to split the light beam into a first beam and a second beam, to direct the first beam to the reference detector, and to direct the second beam through the sample to the signal detector;

(e) a preamplifier connected to the reference detector and a second preamplifier connected to the signal detector to receive an electrical signal thereform which amplifies the electrical signal;

(f) a multiplexer connected to the preamplifier which alternatively sends a signal received through the preamplifier from the reference detector and a signal received through the second preamplifier from the signal detector;

(g) an amplifier connected to receive signals from the multiplexer;

(h) a demodulator connected to receive signals from the amplifier and remove a carrier portion from the signals;

(i) demultiplexer connected to receive signals from the demodulator and which separates the signals;

(j) a differential amplifier connected to receive the reference signal from the demultiplexer and which compares the received signal to a reference voltage and produces an output signal which will continually change until a signal is received from the demultiplexer which equals the reference voltage;

(k) a modulator connected to receive a signal from the differential amplifier and having an output which is connected to the light source in a manner so that the output from the modulator determines intensity of the light beam emitted by the light source;

(l) a signal amplifier connected to the demultiplexer for receiving a signal from the demultiplexer corresponding to the opacity of the sample; and (m) output means connected to receive a signal from the signal amplifier and creates a display corresponding to the signal in a manner selected by an operator to tell the operator the opacity of the sample.

10. The improved transmissometer of claim 9 also comprising a retro-reflector positioned to reflect the second beam back through the sample to the signal detector.

11. The improved transmissometer of claim 9 also comprising a second oscillator connected to the demultiplexer.

12. The improved transmissometer of claim 9 also comprising a window and a second beam splitter positioned to receive the second beam and split the second beam into a third beam which is directed to the signal detector anda fourth beam is directed to the window.

13. The improved transmissometer of claim 12 wherein the second beam splitter is an 80/20 beam splitter.

14. The improved transmissometer of claim 9 wherein the beam splitter is a 50/50 beam splitter.

15. The improved transmissometer of claim 9 wherein the light source is a light emitting diode.

16. The improved transmissometer of claim 13 also comprising an oscillator connected to the modulator and demodulator.

* * * * *

UNITED STATES PATENT AND TRADEMARK OFFICE
CERTIFICATE OF CORRECTION

PATENT NO. : 4,937,461

DATED : June 26, 1990

INVENTOR(S) : JOHN E. TRAINA

It is certified that error appears in the above-identified patent and that said Letters Patent is hereby corrected as shown below:

Column 4, line 62, change "referene" to --reference--.

Column 5, line 7, change "capacity" to --opacity--.

Column 6, line 41, change "anda" to --and a--.

Signed and Sealed this

Third Day of September, 1991

Attest:

HARRY F. MANBECK, JR.

Attesting Officer

Commissioner of Patents and Trademarks